(12) United States Patent
Liou

(10) Patent No.: US 8,790,884 B1
(45) Date of Patent: Jul. 29, 2014

(54) METHOD FOR MEASURING SIALIC ACID IN IMMUNOGLOBULIN G AND IMMUNOGLOBULIN G ANTI-DOUBLE-STRANDED DNA ANTIBODIES

(71) Applicant: Lieh-bang Liou, New Taipei (TW)

(72) Inventor: Lieh-bang Liou, New Taipei (TW)

(73) Assignee: Chang Gung Medical Foundation, Linkou Branch, Taoyuan County (TW)

( * ) Notice: Subject to any disclaimer, the term of this patent is extended or adjusted under 35 U.S.C. 154(b) by 0 days.

(21) Appl. No.: 13/735,046

(22) Filed: Jan. 7, 2013

(51) Int. Cl.
*G01N 33/577* (2006.01)

(52) U.S. Cl.
USPC ............. 435/7.92; 506/9; 506/19; 530/388.1

(58) Field of Classification Search
CPC ........... A61K 2039/505; A61K 39/385; A61K 2039/6031; A61K 31/713; C12P 21/005; G01N 33/6893; G01N 2800/52; G01N 2400/00; G01N 33/6854; G01N 33/5308; G01N 33/57438; G01N 2800/50; G01N 33/56961
See application file for complete search history.

(56) References Cited

PUBLICATIONS

Thompson et al. (Analytical Biochemistry 2011; vol. 413 pp. 114-122).*
Rupin et al., (Journal of immunological methods 1993; vol. 160,pp. 245-252).*
Guhr et al., (PLOS June 20122; vol. 6 issue 6,pp. 1-8).*

* cited by examiner

*Primary Examiner* — Shafiqul Haq
*Assistant Examiner* — Carmencita M Belei
(74) *Attorney, Agent, or Firm* — Che-Yang Chen; Law Office of Michael Chen

(57) ABSTRACT

A method for measuring the amount of sialic acid in immunoglobulin G and immunoglobulin G anti-ds DNA antibodies is disclosed. The method for measuring the amount of sialic acid in immunoglobulin G in the present invention uses culture fluid, blood, plasma, or serum to directly measure the amount of sialic acid in immunoglobulin G. Also, using a mouse monoclonal antibody immunoglobulin G as a standard, which is diluted from 1000 ng/ml to 15.625 ng/ml in phosphate buffered saline (PBS), produces good results. The method for measuring the amount of sialic acid in immunoglobulin G anti-ds DNA antibodies has never been done and the present invention produces good results as well.

2 Claims, 4 Drawing Sheets

METHOD FOR MEASURING SIALIC ACID IN IMMUNOGLOBULIN G AND IMMUNOGLOBULIN G ANTI-DOUBLE-STRANDED DNA ANTIBODIES

FIELD OF THE INVENTION

The present invention relates to a method to measure the amount of sialic acid, and more particular to a method directly using blood, plasma, serum or culture medium to measure the amount of sialic acid of immunoglobulin G (IgG). The present invention also provides a method to measure the sialic acid amount of immunoglobulin G anti-double-stranded DNA antibodies (IgG anti-ds DNA antibodies).

BACKGROUND OF THE INVENTION

Currently, there are two ways to determine the amount of sialic acid of IgG immunoglobulin G: the first one was published 1997 in "The journal of Immunology vol. 159, p. 2327-2333," titled "The Glycosylation of IgA produced by Murine B cells is altered by Th2 cytokines." The steps are as following: Step 1: in enzyme-linked immunosorbent assay (ELISA) plates, adding IgG anti mouse IgG (Fab') 2 fragments into each well; using 0.1% bovine serum albumin in phosphate buffered saline (PBS) washing three times; and adding 1% bovine serum albumin in PBS to prevent non-specific binding; Step 2: after washing three more times, adding different concentrations of IgA obtained from CH12LX cell separation for two hours; Step 3: adding 5 µg/ml of biotinylated Sambucus nigra agglutinin for ninety minutes; Step 4: after washing three more times, adding alkaline phosphate linked avidin (streptavidin) (1 µg/ml) for ninety minutes; and Step 5: finally washing three more times, adding chromogenic substance P-nitrophenyl phosphate disodium, and measuring the absorption value at 405 nm in an enzyme-linked immunosorbent assay (ELISA) reader. This method is disadvantageous because it cannot use culture fluid, blood, plasma, or serum to directly measure the amount of sialic acid in different immunoglobulins (IgG, IgA, IgM).

Another method to measure the sialic acid of immunoglobulin G uses the immunoassay of lectin inhibiting enzyme, published in "The Journal of PLOS ONE, 2011, vol. 6: e21246," titled "Enrichment of sialylated IgG by lectin Fractionation does not enhance the efficacy of immunoglobulin G in a murine model of immune thrombocytopenia." The steps are as following: Step 1: diluting biotinylated Sambucus nigra agglutinin with 0.1% polyoxyethylene (20) sorbitan monolaurate (Tween 20) in PBS to 0.5 µg/ml, the solution mixing with the inhibitor (intravenous immunoglobulin; intravenous immunoglobulin and enriched sialylated IgG; intravenous immunoglobulin containing only desialylated immunoglobulin; and immunoglobulin Fab or immunoglobulin Fc fragments) in a test tube at room temperature for one hour; Step 2: adding intravenous immunoglobulin to an ELISA plate; Step 3: adding the mixture of Step 1 above to the ELISA plate at room temperature for 1 hour; Step 4: After washing, adding streptavidin-linked horseradish peroxidase (at 1:4000 dilution) with 0.1% Tween 20/phosphate buffered saline solution, and incubating the plate at room temperature for one hour; Step 5: After washing, adding 100 µl of tetramethyl benzidine (TMB) substrate buffer (Interchim, Montlucon, Cedex, France) and distilled water into each well, and adding 2 molar (M) concentration of sulfuric acid ($H_2SO_4$) to stop the reaction after 5 minutes; and Step 6: measuring the absorption value at 450 nm in the enzyme-linked immunosorbent assay (ELISA) reader. This method is disadvantageous because there is no sialic acid standard available and it cannot directly measure the amount of sialic acid in different immunoglobulins (IgG, IgA, or IgM).

And in academia or industry, there is no publications related to the measurement of the amount of sialic acid in IgG anti-double-stranded DNA. Therefore, there remains a need for a new and improved method to measure the amount of sialic acid in IgG anti-double-stranded DNA.

SUMMARY OF THE INVENTION

To solve the problems presented above, the present invention provides a method for measuring the amount of sialic acid in IgG and in IgG anti-double-stranded DNA, wherein steps of measuring the amount of sialic acid in IgG includes Step 1: in an ELISA plate, adding 200 ng of Sambucus nigra agglutinin lectin (SNA) dissolved in 100 µl PBS (pH=7.2) in each well, and incubated in a refrigerator at 4° C. overnight; Step 2: washing four times with PBS-0.5% Tween 20, and adding 300 µl of 1% bovine serum albumin dissolved in PBS in each well and incubated at room temperature for 2 hours in order to block non-specific binding; Step 3: washing (four times) the ELISA plate with PBS-0.5% Tween 20 (as used in Step 2), and adding plasma, serum, blood, or the separated immunoglobulin and incubating the plate at room temperature for 2 hours; Step 4: flushing (four times) the ELISA plate with the PBS-0.5% Tween 20, adding 300 µl of 1% bovine serum albumin dissolved in PBS in each well and incubated at room temperature for 1 hour; Step 5: using PBS-0.5% Tween 20 to wash (four times) the ELISA plate, adding 100 µl of horseradish peroxidase-linked goat anti-mouse IgG dissolved in PBS (diluted at 1:8000) in each well, and incubating the plate at room temperature for 1 hour; Step 6: using PBS-0.5% Tween 20 to wash (four times) the plate, adding 100 µl mixture of tetramethyl benzidine (TMB) solution and hydrogen peroxide solution (at equal volume) in each well, incubating the plate at room temperature for 10 minutes, and adding 100 µl of 0.5N $H_2SO_4$ to stop the reaction; and Step 7: measuring the absorption value at 450 nm in each well by an ELISA reader. The measuring method stated above uses mouse monoclonal antibody immunoglobulin G as a standard, diluted from 1000 ng/ml (in PBS) to 15.625 ng/ml.

Another method to measure the amount of sialic acid of immunoglobulin G anti-ds DNA antibodies includes steps of Step 1: in an ELISA plate, adding 150 µl of 0.5 mg/ml of protamine chloride in each well and incubating the plate at room temperature for 2 hours; Step 2: using PBS (pH=7.2) to wash three times and adding 100 µl/well of 50 µg/ml calf thymus double-stranded DNA overnight at 4° C.; Step 3: preparing oxidized bovine serum albumin, by dissolving bovine serum albumin in 20 mM potassium periodate (in PBS, pH=7.2) and 50 mM sodium acetate (final pH=4.0) at 4° C. (for 30 minutes) to obtain a mixture, and the mixture is dialyzed with tris-buffered saline (pH=7.4), and finally adding (0.1% by volume) of Tween 20 solution to make 1% oxidized bovine serum albumin; Step 4: using PBS-0.5% Tween 20 as a washing fluid to wash the ELISA plate (four times), adding 300 µl of 1% oxidized bovine serum albumin into each well and incubating the plate at room temperature for 2 hours, in order to block non-specific binding; Step 5: washing (four times) the ELISA plate in Step 4 with PBS-0.5% Tween 20, adding 100 µl of IgG isolated from a protein G column, and incubating the plate at room temperature for two hours; Step 6: washing (four times) the ELISA plate with PBS-0.5% Tween 20, adding 100 µl of diluted (at 1:500 dilution) horseradish peroxidase-SNA lectin to each well;

Step 7: washing (four times) the ELISA plate with PBS-0.5% Tween 20, adding 100 µl of TMB solution and hydrogen peroxide solution mixture (at equal volume) at room temperature for 5 minutes, and adding 100 µl of 0.5N $H_2SO_4$ into each well to stop the reaction; Step 8: measuring the absorption value at 450 nm in each well by an ELISA reader. The measuring method stated above uses a mouse monoclonal IgG anti-double-stranded DNA antibody as a standard, diluted from 1000 ng/ml (in PBS) to 15.625 ng/ml and incubated at room temperature for two hours.

The present invention provides a method for measuring the amount of sialic acid in immunoglobulin G to directly measure the amount of sialic acid using blood, plasma, serum or culture medium. Also, the present invention also uses mouse monoclonal immunoglobulin G and mouse monoclonal immunoglobulin G double-stranded DNA antibodies as a standard, diluted from 1000 ng/ml (in PBS) to 15.625 ng/ml at the room temperature for two hours, which shows good experimental results.

In addition, the present invention can be used to detect lupus proteinuria and the degree of pathological destruction of lupus nephritis, especially before the situation of lupus proteinuria becomes worse by measuring the amount of sialic acid in immunoglobulin G and immunoglobulin G anti-ds DNA antibodies. The aggravation of lupus nephritis can be avoided by increasing the dose of steroid or immunosuppressive drugs.

DETAILED DESCRIPTION OF THE INVENTION

Figure 1:
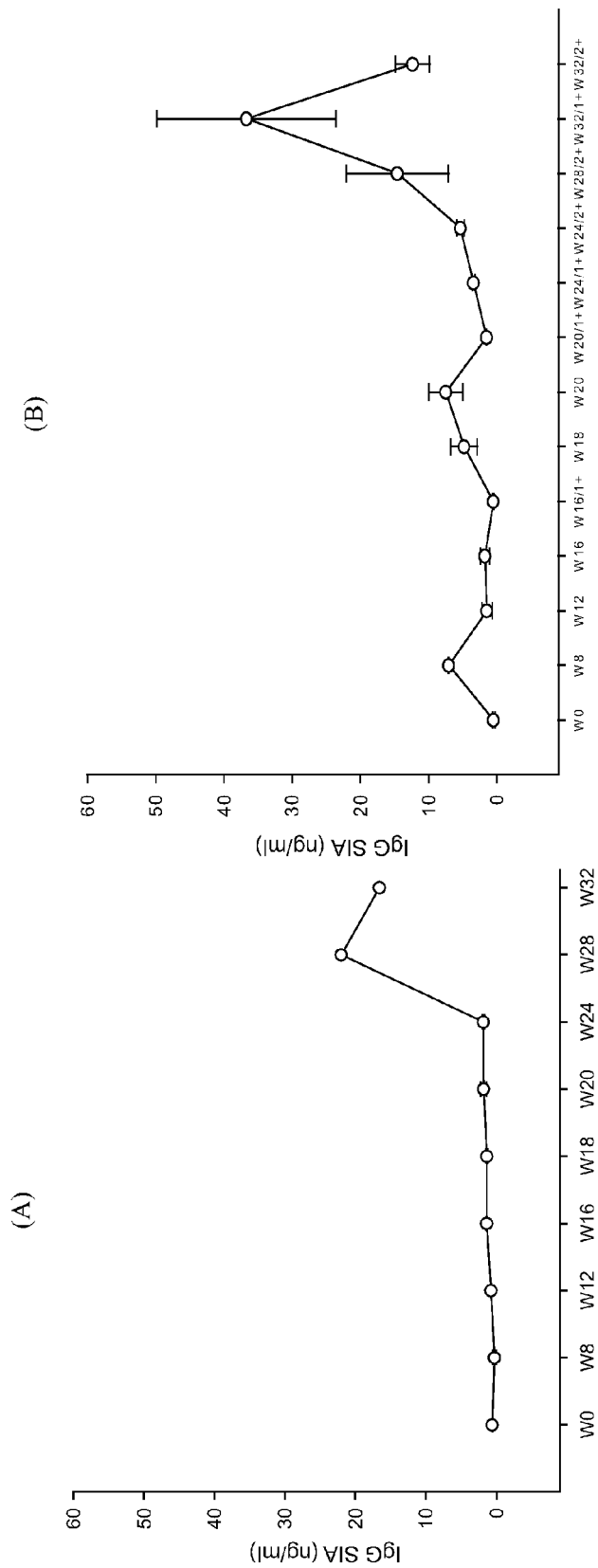
FIG. 1 shows changes of IgG α2,6-sialic acid (SIA) amounts over time and comparison between PBS-injected BALB/c mice and positive-proteinuria groups in pristane-injected BALB/c mice.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention provides a method for measuring the amount of sialic acid in immunoglobulin G and immunoglobulin G anti-ds DNA antibodies, the method for measuring the amount of sialic acid in immunoglobulin G comprising steps of:

Step 1: in an ELISA plate containing 96 wells, adding 200 ng of *Sambucus nigra* agglutinin lectin (SNA) dissolved in 100 µl PBS (pH=7.2) in each well, and incubating the plate in a refrigerator at 4° C. overnight;

Step 2: washing four times with PBS-0.5% with polyoxyethylene (20) sorbitan monolaurate (Tween 20) as a rinse solution, and adding 300 µl of 1% bovine serum albumin (BSA) dissolved in PBS in each well and incubating the plate at room temperature for 2 hours in order to block non-specific binding;

Step 3: washing (four times) the ELISA plate with PBS-0.5% Tween 20 (as used in Step 2), and adding plasma, serum, blood, or the separated immunoglobulin and incubating the plate at room temperature for 2 hours;

Step 4: washing (four times) the ELISA plate with the PBS-0.5% Tween 20, adding 300 µl of 1% bovine serum albumin dissolved in PBS in each well and incubating the plate in room temperature for 1 hour;

Step 5: using PBS-0.5% Tween 20 to wash (four times) the ELISA plate, adding 100 µl of horseradish peroxidase-linked goat anti-mouse immunoglobulin G dissolved in PBS (at 1:8000 dilution), and incubating the plate in a room temperature for 1 hour;

Step 6: using PBS-0.5% Tween 20 to wash (four times) the ELISA plate, adding 100 µl mixture of tetramethyl benzidine (TMB) solution and hydrogen peroxide solution (at equal volume) in each well, incubating the plate at room temperature for 10 minutes, and adding 100 µl of 0.5N $H_2SO_4$ to stop the reaction; and Step 7: measuring the absorption value at 450 nm in each well by an ELISA reader. The measuring method stated above uses a mouse monoclonal antibody immunoglobulin G as a standard, diluted from 1000 ng/ml, 500 ng/ml, 250 ng/ml, 125 ng/ml, 61.5 ng/ml, 31.25 ng/ml (in PBS) to 15.625 ng/ml and incubated at room temperature for two hours.

Furthermore, the method for measuring the amount of sialic acid in immunoglobulin G anti-ds DNA antibodies comprises steps of:

Step 1: in an ELISA plate containing 96 wells, adding 150 µl of 0.5 mg/ml of protamine chloride in each well and incubating the plate at room temperature for 2 hours;

Step 2: washing (three times) with PBS (pH=7.2) and adding 100 µl/well of 50 µg/ml calf thymus double-stranded DNA overnight at 4° C.;

Step 3: preparing oxidized bovine serum albumin, wherein the bovine serum albumin is dissolved in 20 mM potassium periodate (PBS, pH=7.2) and 50 mM sodium acetate (final pH=4.0) at 4° C. (for 30 minutes) to obtain a mixture, and the mixture is dialyzed with tris-buffered saline (pH=7.4), and finally adding (0.1% by volume) of polyoxyethylene (20) sorbitan monolaurate (Tween 20) solution to make 1% oxidized bovine serum albumin;

Step 4: using PBS-0.5% Tween 20 to wash the ELISA plate (four times), adding 300 µl of 1% oxidized bovine serum albumin into each well and incubating the plate at room temperature for 2 hours in order to block non-specific binding;

Step 5: washing (four times) the ELISA plate in Step 4 with PBS-0.5% Tween 20, adding 100 µl of immunoglobulin G isolated from a protein G column, and incubating the plate at room temperature for two hours;

Step 6: washing (four times) the ELISA plate in Step 4 with PBS-0.5% Tween 20, adding 100 µl of diluted (at 1:500 dilution) horseradish peroxidase-linked *Sambucus nigra* agglutinin lectin (SNA) to each well;

Step 7: washing (four times) the ELISA plate with PBS-0.5% Tween 20, adding 100 µl of TMB solution and peroxide hydrogen solution mixture (at equal volume) in each well at room temperature for 5 minutes, and adding 100 µl of 0.5N $H_2SO_4$ into each well to stop the reaction;

Step 8: measuring the absorption value at 450 nm in each well by an ELISA reader.

The measuring method stated above uses mouse monoclonal immunoglobulin G anti-ds DNA antibodies as a standard, diluted from 1000 ng/ml (in PBS), 500 ng/ml, 250 ng/ml, 125 ng/ml, 61.5 ng/ml, 31.25 ng/ml to 15.625 ng/ml and incubated at room temperature for two hours.

Referring to FIG. 1, the result shows changes of IgG α2,6-sialic acid (SIA) amounts over time and comparison between PBS-injected BALB/c mice and positive-proteinuria groups in pristane-injected BALB/c mice. W0 indicates the time when BALB/c mice at 8-week-old were injected with PBS (diagram (A)) or pristane (diagram (B)). Blood was obtained at indicated time points. IgG SIA levels were determined by ELISA assay with standards of AF1.9-L2 (mouse monoclonal IgG) at various dilutions. B. Comparison of IgG SIA amounts between non-proteinuria groups and proteinuria (1+ or 2+) groups (lower SIA levels) in pristane-injected BALB/c mice rendered P<0.001 and F=7.562 (by ANOVA). W16 represented those mice sacrificed at week 16 with no proteinuria and W16/1+ represented those mice sacrificed at week 16 with 1+ proteinuria. IgG SIA amounts of W16/1+ proteinuria mice (lower) vs. W16 non-proteinuria mice yielded P=0.788 (by LSD). IgG SIA amounts of W20/1+ proteinuria mice (lower) vs. W20 non-proteinuria mice gave P=0.199 (by LSD). IgG SIA amounts of W32/2+ proteinuria mice (lower) vs. W32/1+ proteinuria mice rendered P<0.001 (by LSD).

Figure 2:
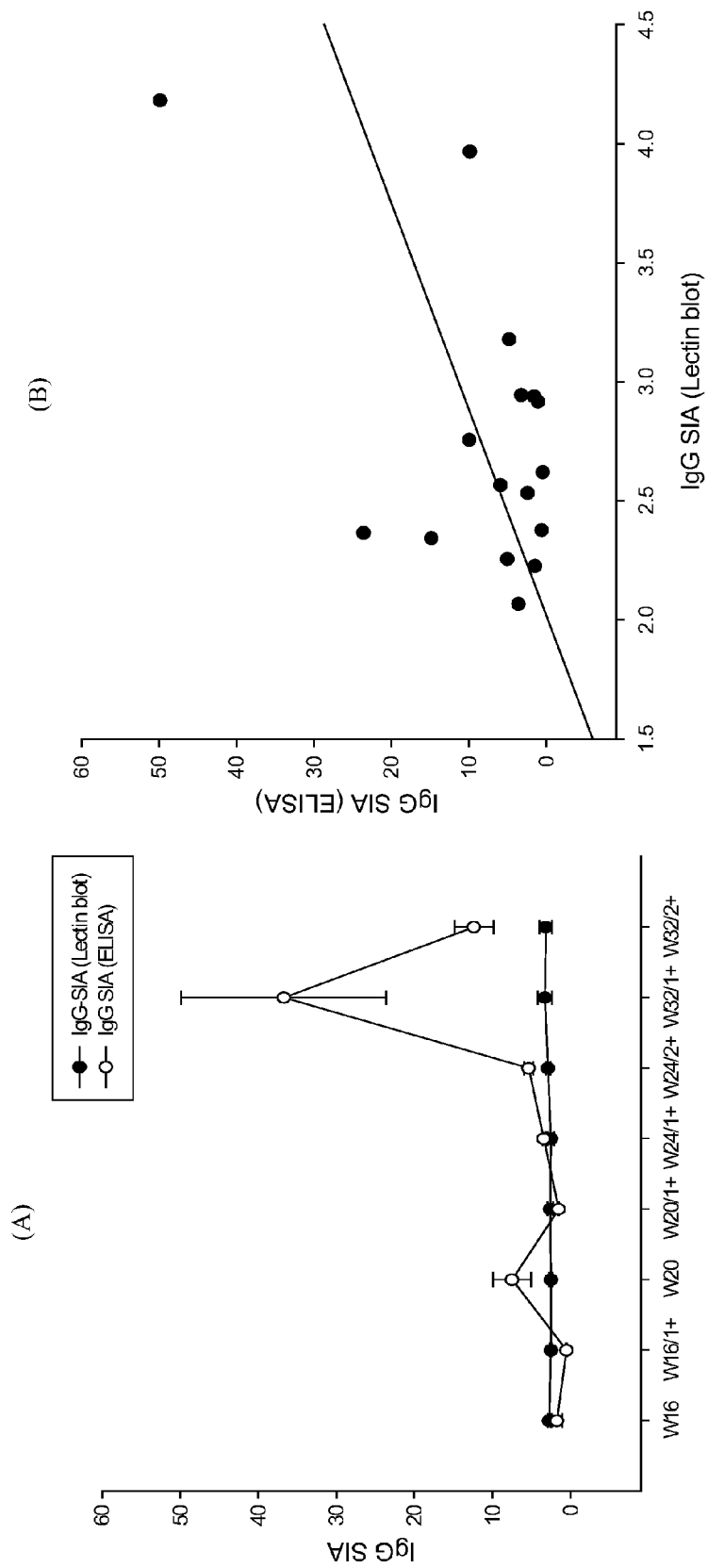
FIG. 2 shows correlation of α2,6-sialic acid (SIA) amounts of mouse IgG between in the ELISA assay and in the lectin blot.

Referring to FIG. 2, the result shows correlation of α2,6-sialic acid (SIA) amounts of mouse IgG between in the ELISA assay and in the lectin blot. BALB/c mice were injected with pristane intra-peritoneally and blood was obtained from week 16 until week 32. Definitions for different time points were the same as those in FIG. 1. Diagram (A) in FIG. 2 shows SIA levels of mouse IgG over time. IgG SIA units for the ELISA assay were based on AF1.9-L2 IgG amounts in ng/ml. IgG SIA units for the lectin blots were based on the density taken. Diagram (B) in FIG. 2 shows the correlation curve of mouse IgG SIA amounts between in the ELISA assay and in the lectin blot. r=0.548 and P=0.028.

Figure 3:
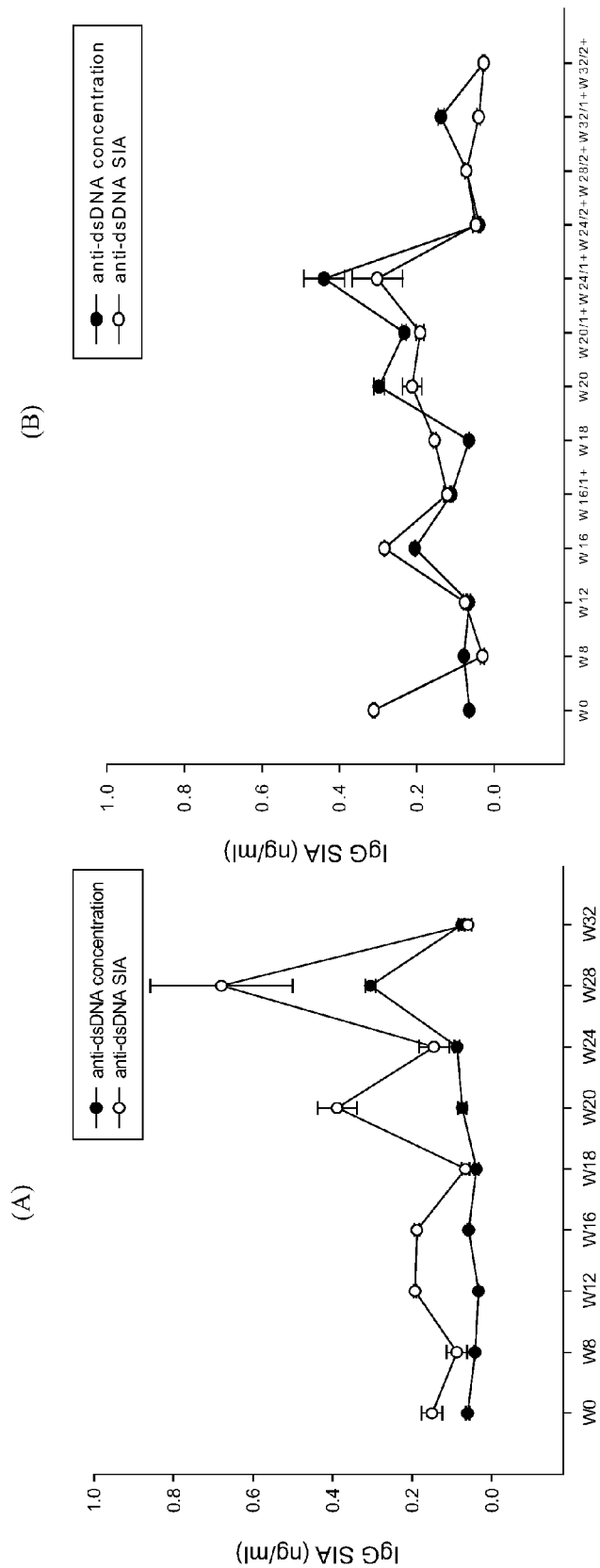
FIG. 3 shows changes of α2,6-sialic acid (SIA) amounts of IgG anti-ds DNA over time and comparison between PBS-injected BALB/c mice and positive-proteinuria groups in pristane-injected BALB/c mice.

Referring to FIG. 3, the result shows changes of α2,6-sialic acid (SIA) amounts of IgG anti-ds DNA over time and comparison between PBS-injected BALB/c mice and positive-proteinuria groups in pristane-injected BALB/c mice. W0 indicates the time when BALB/c mice aged 8 week-old were injected with PBS (diagram (A)) or pristane (diagram (B)). Blood was obtained at indicated time points. In FIG. 3, the comparison of IgG anti-ds DNA levels and SIA amounts of IgG anti-ds DNA between non-proteinuria groups and proteinuria groups (1+ or 2+) in pristane-injected BALB/c mice rendered P<0.001 and F=78.463, and P<0.001 and F=21.489, respectively (by ANOVA). SIA amounts of IgG anti-ds DNA in W16/1+ proteinuria mice were lower than W16 non-proteinuria mice (P=0.002 by LSD). SIA amounts of IgG anti-ds DNA in W20/1+ proteinuria mice were lower than W20 non-proteinuria mice (P=0.656 by LSD). SIA amounts of IgG anti-ds DNA in W24/1+ proteinuria mice were lower than W24 non-proteinuria mice (P<0.001 by LSD). SIA amounts of IgG anti-ds DNA in W32/2+ proteinuria mice were lower than W32/1+ proteinuria mice (P<0.770 by LSD).

Figure 4:
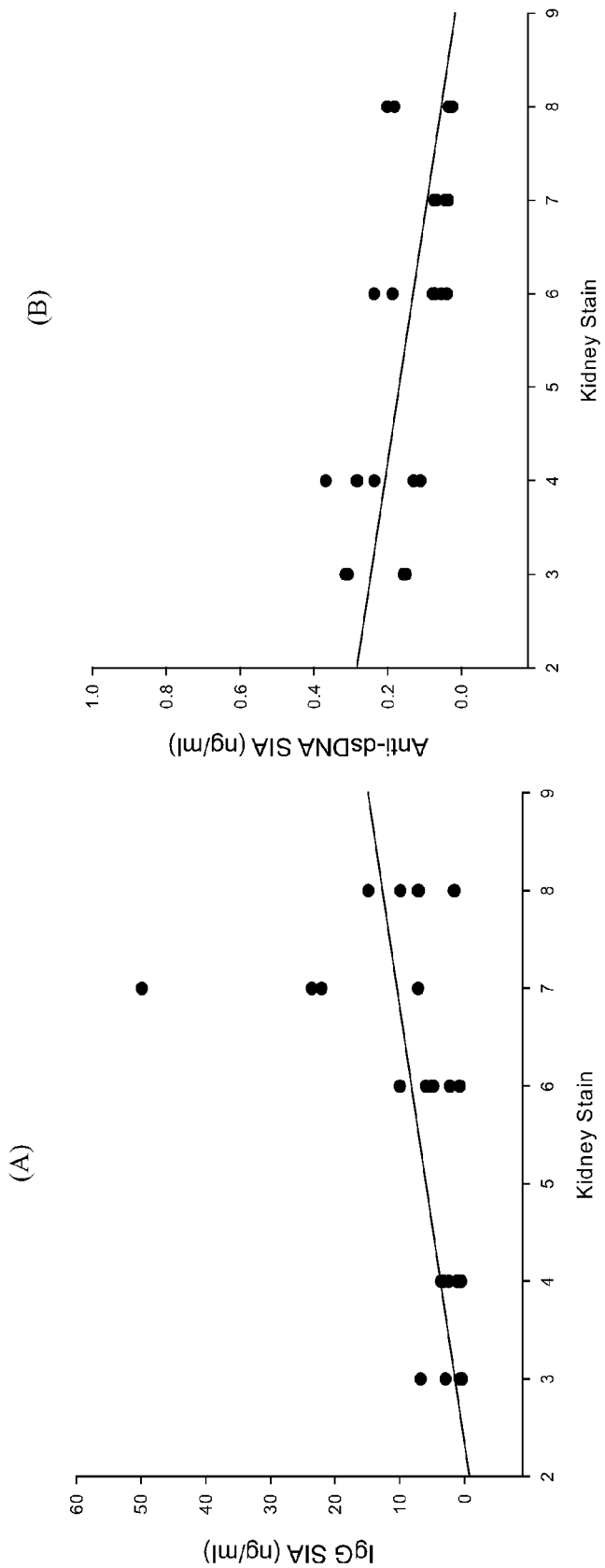
FIG. 4 shows correlation of the C3 staining of kidney tissues and plasma IgG sialyation in pristane-injected BALB/c mice.

Referring to FIG. 4, the result shows correlation of the C3 staining of kidney tissues and plasma IgG sialyation levels in pristane-injected BALB/c mice. Two renal tissues were taken from each time points (week 0, 8, 12, 16, 18, 20, 24, 28 and 32) and stained with anti-C3 antibody. Grading was established as 0 (background with a secondary antibody only), 1−, 1+, 2−, 2+, 3−, 3+, 4− and 4+ with 8 grades in total. Diagram (A) in FIG. 4 shows the correlation between the C3 staining of renal tissues and IgG-SIA levels yielded Spearman's rho=0.560, and P=0.003. Diagram (B) in FIG. 4 shows the correlation between the C3 staining of renal tissues and SIA levels of IgG anti-ds DNA antibodies rendered Spearman's rho=0.676, and P<0.001.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A method for measuring the absolute amount of sialic acid in immunoglobulin G anti-double-stranded DNA antibodies comprises steps of:

Step 1: in an enzyme immunoassay petridish, adding 150 µl of 0.5 mg/ml of protamine chloride in each grid and placing said petridish at room temperature for 2 hours;

Step 2: washing (three times) with PBS (pH=7.2) and adding 100 µl of 50 µg/ml calf thymus double-stranded DNA overnight at 4° C.;

Step 3: preparing oxidized bovine serum albumin, wherein the bovine serum albumin is dissolved in 20 mM potassium periodate (PBS, pH=7.2) and 50 mM sodium acetate (final pH=4.0 of the mixture of sodium periodate and sodium acetate) at 4° C. (for 30 minutes) to obtain a mixture, and the mixture is dialyzed with tris-buffered saline (pH=7.4), and adding (0.1% by volume) of polyoxyethylene (20) sorbitan monolaurate solution to make 1% oxidized bovine serum albumin;

Step 4: using PBS-0.5% Tween 20 as a flushing fluid to flush the enzyme immunoassay petridish (four times), adding 300 µl of 1% of oxidation bovine serum albumin into each grid, and placing said petridish at room temperature for 2 hours in order to block non-specific adhesion;

Step 5: washing (four times) the enzyme immunoassay petridish as in Step 4 with PBS-0.5% Tween 20, adding 100 µl of immunoglobulin G isolated from protein G, and placing said petridish at room temperature for two hours;

Step 6: washing (four times) the enzyme immunoassay petridish as in Step 4 with PBS-0.5% Tween 20, and adding diluted (500 times) horseradish peroxidase-linked *sambucus nigra* agglutinin lectin (SNA) 100 µl to each grid;

Step 7: washing (four times) the enzyme immunoassay petridish as in Step 4 with PBS-0.5% Tween 20, adding mixture of tetramethyl benzidine solution 50 µl and peroxide hydrogen solution 50 μl at room temperature for 5 minutes, and adding 100 μl of 0.5N $H_2SO_4$ into each grid to prevent the reaction; and Step 8: measuring the absorption value at 450 nm in each grid in the enzyme immunoassay analyzer, wherein a mouse monoclonal antibody immunoglobulin G anti-double-stranded DNA is used as a standard, which is diluted from 1000 ng/ml to 15.625 ng/ml and placed at room temperature for two hours.

2. The method for measuring the amount of sialic acid in immunoglobulin G anti-double-stranded DNA antibodies of claim 1, wherein said enzyme immunoassay petridish has ninety-six (96) grids.

* * * * *